(12) United States Patent
Markosyan et al.

(10) Patent No.: US 12,049,674 B2
(45) Date of Patent: *Jul. 30, 2024

(54) STEVIA CULTIVAR '16228013'

(71) Applicant: PureCircle USA Inc., Westchester, IL (US)

(72) Inventors: Avetik Markosyan, Bandar Enstek (MY); Seong Siang Ong, Bandar Enstek (MY); Runchun Jing, Ganzhou (CN); Yu Cheng Bu, Ganxian (CN); Juan Zhu, NanChang (CN); Jian Ning Chen, Ganxian (CN); Yeen Yee Wong, Negeri Sembilan (MY)

(73) Assignee: PureCircle USA Inc., Westchester, IL (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/700,817

(22) Filed: Mar. 22, 2022

(65) Prior Publication Data

US 2022/0210991 A1    Jul. 7, 2022

Related U.S. Application Data

(63) Continuation of application No. 16/769,984, filed as application No. PCT/US2018/064532 on Dec. 7, 2018, now Pat. No. 11,284,578.

(60) Provisional application No. 62/595,609, filed on Dec. 7, 2017.

(51) Int. Cl.
  *C12Q 1/6895* (2018.01)
  *A01H 5/12* (2018.01)
  *A01H 6/14* (2018.01)
  *G16B 20/20* (2019.01)

(52) U.S. Cl.
  CPC .......... *C12Q 1/6895* (2013.01); *A01H 5/12* (2013.01); *A01H 6/1488* (2018.05); *G16B 20/20* (2019.02)

(58) Field of Classification Search
  None
  See application file for complete search history.

(56) References Cited

U.S. PATENT DOCUMENTS

| 11,284,578 B2 | 3/2022 | Markosyan et al. |
| 2012/0151635 A1 | 6/2012 | Coruzzi et al. |
| 2014/0283217 A1 | 9/2014 | Coruzzi et al. |
| 2015/0067923 A1 | 3/2015 | Coruzzi et al. |
| 2016/0057955 A1 | 3/2016 | Li et al. |
| 2016/0057965 A1 | 3/2016 | Li et al. |
| 2016/0057966 A1 | 3/2016 | Li et al. |
| 2021/0259184 A1* | 8/2021 | Markosyan .............. A01H 1/04 |
| 2022/0338436 A1* | 10/2022 | Markosyan .............. A01H 5/12 |
| 2022/0338437 A1* | 10/2022 | Markosyan .............. A01H 5/12 |

FOREIGN PATENT DOCUMENTS

| CN | 103667343 A | 3/2014 |
| WO | WO2016127075 A2 | 8/2016 |

OTHER PUBLICATIONS

Latham, J.R., et al., "The Mutational Consequences of Plant Transformation" J. of Biomedicine and Biotechnology. Hindwi Publishing Company. Article ID 25376. pp. 1-7 (2006).
Non-final Office Action dated Jun. 3, 2021 for U.S. Appl. No. 16/769,984 (now U.S. Pat. No. 11,284,578), 17 pages.
Response to Office Action filed on Sep. 3, 2021 for U.S. Appl. No. 16/769,984 (now U.S. Pat. No. 11,284,578), 11 pages.
Notice of Allowance dated Nov. 22, 2021 for U.S. Appl. No. 16/769,984 (now U.S. Pat. No. 11,284,578), 16 pages.
Office Action dated Jul. 26, 2022 for ARIPO Application No. AP/P/2020/012512, 4 pages.
Office Action dated Mar. 2, 2022 for China Application No. 201880078952.1 and Response filed on Jul. 15, 2022, 23 pages.
Voluntary amendment of claims filed on Aug. 18, 2022 for China Application No. 201880078952.1, 3 pages.
Extended Search Report dated Aug. 13, 2021 for European Application No. 18887016.6 and Response filed on Feb. 11, 2022, 6 pages.
Examination Report dated May 10, 2022 for European Application No. 18887016.6, 5 pages.

* cited by examiner

*Primary Examiner* — Weihua Fan
(74) *Attorney, Agent, or Firm* — Weatherly IP Solutions, LLC; James M. Weatherly

(57) ABSTRACT

A stevia cultivar, designated '16228013', is disclosed. Further embodiments relate to the plant parts of stevia cultivar '16228013', to the plants of stevia '16228013' and to methods for producing a stevia plant produced by crossing the cultivar '16228013' with itself or another stevia variety, including methods using marker assisted breeding. Further embodiments relate to hybrid stevia seeds and plants produced by crossing the cultivar '16228013' with another stevia cultivar. Six highly polymorphic SNPs loci and the corresponding genomic sequences used to identify plant variety '16228013' derived plant materials are also disclosed.

1 Claim, 1 Drawing Sheet

Specification includes a Sequence Listing.

| SEQ ID NO; SNP No: | Sequences |
|---|---|
| SEQ ID NO:1; SNP No: 1 | AAAAATAGACTTTTTACCATCTCTTCCTCTCAAGTCTCAATCTCAACACCTACACR TGTATGTTTTTTCAAACAAACCACACACATTGGTTTTGATCTAAAA<br>Where "R" can either be "G" or "A" |
| SEQ ID NO: 2; SNP No: 2 | GGTAATAACAACCTTAGTTGCCTAATTATATATGCTTCTTGTGATGAATTTCCAATCT AAYTGTACTTGAGCTAATATAGAAAACCTAGTTGCTGCCACATT<br>Where "Y" can either be "C" or "T" |
| SEQ ID NO: 3; SNP No: 3 | GATTGGTAATTGGAAGTGTTGTTTATTACATATGGCAAGAGAGGAACCTTASATTG TTTCAAGGTAAGTCTCGTGGTTATGATGATGTGTGCAAG<br>Where "S" can either be "G" or "C" |
| SEQ ID NO: 4; SNP No: 4 | AAAATGGAAACATTTTCTTTTTACATTTCAGCATCTGAGTTGACTCGGYTGCAATC ACAAATATGTGGAAAAAATGGTGATCACCAAGTTCCAGAGTT<br>Where "Y" can either be "T" or "C" |
| SEQ ID NO: 5; SNP No: 5 | ATGGAAGATGAACCTGATGTTCCTGAACAACTCGTTCGCCGATCGGTTWGTCTCG AAATCCATTCACAAGTTCTTTTATATTGCACTGATTTGATACTTAGGG<br>Where "W" can either be "A" or "T" |
| SEQ ID NO: 6; SNP No: 6 | AGAAGAACAGTGCCAGAATAATCTGTGGCGCTAAAGTGATCCAACCAYACCCTTG TTCTCCCAGTTATATAAAAGATTAAAAATTGCTAGTTGTCCTTCGC<br>Where "Y" can either be "C" or "T" |

STEVIA CULTIVAR '16228013'

CROSS-REFERENCE TO RELATED APPLICATIONS

This application is a Continuation Application which claims the benefit of priority to U.S. application Ser. No. 16/769,984, filed on Jun. 4, 2020, which is a 371 National Stage entry of and claims the benefit of priority from International Application No. PCT/US2018/064532 filed on Dec. 7, 2018, which claims the benefit of priority to U.S. Provisional Patent Application No. 62/595,609, filed on Dec. 7, 2017, the contents of which are incorporated herein by reference in their entireties.

SUBMISSION OF SEQUENCE LISTING

The Sequence Listing associated with this application is filed in electronic format via EFS-Web and is hereby incorporated by reference into the specification in its entirety.

BACKGROUND

All publications cited in this application are herein incorporated by reference.

The present disclosure relates to a stevia (*Stevia rebaudiana*) seed, a stevia plant, a stevia cultivar, and a stevia hybrid. This disclosure further relates to a method for producing stevia seed and plants. All publications cited in this application are herein incorporated by reference. Stevia is an important and valuable field crop for the production of sweeteners, sugar substitutes, and other consumable ingredients. Thus, a continuing goal of stevia plant breeding is to develop stable, high yielding stevia cultivars of stevia species that are agronomically sound. The reasons for this goal are to maximize the amount and quality of the sweeteners, sugar substitutes, and other consumable ingredients. To accomplish this goal, the stevia breeder must select and develop plants that have the traits that result in superior cultivars.

The development of new stevia cultivars requires the evaluation and selection of parents and the crossing of these parents. The lack of predictable success of a given cross requires that a breeder, in any given year, make several crosses with the same or different breeding objectives.

The foregoing examples of the related art and limitations related therewith are intended to be illustrative and not exclusive. Other limitations of the related art will become apparent to those of skill in the art upon a reading of the specification.

SUMMARY

It is to be understood that the embodiments include a variety of different versions or embodiments, and this Summary is not meant to be limiting or all-inclusive. This Summary provides some general descriptions of some of the embodiments, but may also include some more specific descriptions of other embodiments.

The following embodiments and aspects thereof are described in conjunction with systems, tools, and methods, which are meant to be exemplary and illustrative, not limiting in scope. In various embodiments, one or more of the above-described problems have been reduced or eliminated, while other embodiments are directed to other improvements.

One or more embodiments relate to a stevia seed, a stevia plant, a stevia cultivar, and a method for producing a stevia plant.

One or more embodiments further relates to a method of producing stevia seeds and plants by crossing a plant of the instant invention with another stevia plant.

One embodiment relates to plant tissue such as shoots, microshoots and seed of the stevia variety '16228013'. Another aspect also relates to plants produced by growing the seed of the stevia variety '16228013', as well as the derivatives of such plants. As used herein, the term "plant" includes plant cells, plant protoplasts, plant cells of a tissue culture from which stevia plants can be regenerated, plant calli, plant clumps, shoots, microshoots and plant cells that are intact in plants or parts of plants, such as pollen, flowers, seeds, leaves, stems, and the like.

Another embodiment relates to a tissue culture of regenerable cells of the stevia variety '16228013', as well as plants regenerated therefrom, wherein the regenerated stevia plant expresses all the physiological and morphological characteristics of a plant grown from the stevia seed or tissue culture designated '16228013'.

Yet another embodiment is a stevia plant of the stevia variety '16228013' comprising at least a first transgene, wherein the stevia plant is otherwise capable of expressing all the physiological and morphological characteristics of the stevia variety '16228013'. In particular, embodiments of the invention, a plant is provided that comprises a single locus conversion. A single locus conversion may comprise a transgenic gene, which has been introduced by genetic transformation into the stevia variety '16228013' or a progenitor thereof. A transgenic or non-transgenic single locus conversion can also be introduced by backcrossing, as is well known in the art. In certain embodiments, the single locus conversion may comprise a dominant or recessive allele. The locus conversion may confer potentially any desired trait upon the plant as described herein.

Yet another embodiment is about using the other New Plant Breeding Techniques (NPBT), such as Oligo-Directed Mutagenesis (ODM) and CRISPR-Cas9 or CRISPR-Cpf1, to modify the stevia variety '16228013' or a progenitor thereof.

Still yet, another embodiment relates to a first generation ($F_1$) hybrid stevia seed produced by crossing a plant of the stevia variety '16228013' to a second stevia plant. Also included in the embodiments of the invention are the $F_1$ hybrid stevia plants grown from the hybrid seed produced by crossing the stevia variety '16228013' to a second stevia plant. Still further included in the embodiments of the invention are the seeds of an $F_1$ hybrid plant produced with the stevia variety '16228013' as one parent, the second generation ($F_2$) hybrid stevia plant grown from the seed of the $F_1$ hybrid plant, and the seeds of the $F_2$ hybrid plant.

Still yet, another embodiment is a method of producing stevia seeds comprising crossing a plant of the stevia variety '16228013' to any second stevia plant, including itself or another plant of the variety '16228013'. In particular, embodiments of the invention, the method of crossing comprises the steps of: (a) planting seeds of the stevia variety '16228013'; (b) cultivating stevia plants resulting from said seeds until said plants bear flowers; (c) allowing fertilization of the flowers of said plants; and (d) harvesting seeds produced from said plants.

Still yet another embodiment is a method of producing hybrid stevia seeds comprising crossing the stevia variety '16228013' to a second, distinct stevia plant which is non-isogenic to the stevia variety '16228013'. In particular, where the crossing comprises the steps of: (a) planting seeds of stevia variety '16228013' and a second, distinct stevia plant; (b) cultivating the stevia plants grown from the seeds until the plants bear flowers; (c) cross pollinating a flower on one of the two plants with the pollen of the other plant; and (d) harvesting the seeds resulting from the cross pollinating.

Still yet another embodiment is a method for developing a stevia plant in a stevia breeding program comprising: (a) obtaining a stevia plant, or its parts, of the variety '16228013'; and (b) employing said plant or parts as a source of breeding material using plant breeding techniques. In the method, the plant breeding techniques may be selected from the group consisting of recurrent selection, mass selection, bulk selection, backcrossing, pedigree breeding, marker-assisted selection, genetic transformation and genome editing. In certain embodiments, the stevia plant of variety '16228013' is used as the male or female parent.

Still yet another embodiment is a method of producing a stevia plant derived from the stevia variety '16228013', the method comprising the steps of: (a) preparing a progeny plant derived from stevia variety '16228013' by crossing a plant of the stevia variety '16228013' with a second stevia plant; and (b) crossing the progeny plant with itself or a second plant to produce a progeny plant of a subsequent generation which is derived from a plant of the stevia variety '16228013'. In one embodiment, the method further comprises: (c) crossing the progeny plant of a subsequent generation with itself or a second plant; and (d) repeating steps (b) and (c) for at least 2-10 additional generations to produce an inbred stevia plant derived from the stevia variety '16228013'. Also provided is a plant produced by this and the other methods of the embodiments of the invention.

Plant variety '16228013'-derived plants produced by this and the other methods of the embodiments of the invention described herein may, in certain embodiments, be further defined as comprising the traits of plant variety '16228013' given in Table 1.

In another embodiment, a method of vegetatively propagating the stevia plant of the present application, comprising the steps of: (a) collecting tissue or cells capable of being propagated from a plant of '16228013'; (b) cultivating said tissue or cells of (a) to obtain proliferated shoots; and (c) rooting said proliferated shoots to obtain rooted plantlets; or (d) cultivating said tissue or cells to obtain proliferated shoots, or to obtain plantlets. Further, plants produced by growing said plantlets or proliferated shoots are provided for.

In another embodiment, a method of using single nucleotide polymorphisms (SNPs) markers to identify *Stevia rebaudiana* variety is described. Six highly polymorphic SNPs loci and the corresponding genomic sequences are used to identify plant variety '16228013'-derived plant materials. The genomic sequences with the marked six SNPs are listed in Table 4.

The use of the word "a" or "an" when used in conjunction with the term "comprising" in the claims and/or the specification may mean "one," but it is also consistent with the meaning of "one or more," "at least one," and "one or more than one."

Other objects, features, and advantages may become apparent from the following detailed description. It should be understood, however, that the detailed description and the specific examples, while indicating specific embodiments, are given by way of illustration only, since various changes and modifications within the spirit and scope of the embodiments of the invention may become apparent to those skilled in the art from this detailed description.

Another embodiment provides regenerable cells for use in tissue culture of stevia plant '16228013'. The tissue culture may be capable of regenerating plants having the physiological and morphological characteristics of the foregoing stevia plant, and of regenerating plants having substantially the same genotype as the foregoing stevia plant. The regenerable cells in such tissue cultures may be embryos, protoplasts, meristematic cells, callus, pollen, leaves, anthers, pistils, roots, root tips, flowers, seeds, or stems. Still further, another embodiment provides stevia plants regenerated from the tissue cultures of the invention.

Another embodiment of the present invention comprises a method for developing a stevia plant in a stevia plant breeding program, comprising applying plant breeding techniques comprising recurrent selection, backcrossing, pedigree breeding, marker enhanced selection, haploid/double haploid production, or transformation to the stevia plant of claim 1, or its parts, wherein application of said techniques results in development of a stevia plant.

Another embodiment of the present invention comprises a second stevia seed, plant, plant part, or cell produced by crossing a plant or plant part of stevia cultivar '16228013', or a locus conversion thereof, with another plant, wherein representative plant tissue of said stevia cultivar '16228013' has been deposited under CGMCC No. 16984 and wherein said stevia cultivar '16228013' seed, plant, plant part, or cell has the same polymorphisms for the single nucleotide polymorphisms of SNP ID NO:1, SNP ID NO:2, SNP ID NO:3, SNP ID NO:4, SNP ID NO:5, and SNP ID NO:6 as the plant or plant part of stevia cultivar '16228013'.

Still yet another embodiment is the six single nucleotide polymorphisms used to identify the said stevia cultivar '16228013', including the locus-specific genomic sequences and the identified single nucleotide polymorphisms within the sequences.

In addition to the exemplary aspects and embodiments described above, further aspects and embodiments may become apparent by study of the following descriptions.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, "sometime" means at some indefinite or indeterminate point of time. So for example, as used herein, "sometime after" means following, whether immediately following or at some indefinite or indeterminate point of time following the prior act.

Various embodiments are set forth in the Detailed Description as provided herein and as embodied by the claims. It should be understood, however, that this Summary does not contain all of the aspects and embodiments, is not meant to be limiting or restrictive in any manner, and that embodiment(s) as disclosed herein is/are understood by those of ordinary skill in the art to encompass obvious improvements and modifications thereto.

In addition to the exemplary aspects and embodiments described above, further aspects and embodiments will become apparent by study of the following descriptions.

BRIEF DESCRIPTION OF THE SEQUENCE LISTINGS

SEQ ID NO: 1 discloses a single nucleotide polymorphism "stv_snp_568899", which is highly polymorphic in the tested Stevia lines.

SEQ ID NO: 2 discloses a single nucleotide polymorphism "stv_snp_77072", which is highly polymorphic in the tested Stevia lines.

SEQ ID NO: 3 discloses a single nucleotide polymorphism "stv_snp_11466", which is highly polymorphic in the tested Stevia lines.

SEQ ID NO: 4 discloses a single nucleotide polymorphism "stv_snp_14413", which is highly polymorphic in the tested Stevia lines.

SEQ ID NO: 5 discloses a single nucleotide polymorphism "stv_snp_6645712", which is highly polymorphic in the tested Stevia lines.

SEQ ID NO: 6 discloses a single nucleotide polymorphism "stv_snp_682884", which is highly polymorphic in the tested Stevia lines.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1 shows the SNP sequences for SEQ ID Nos.: 1-6.

DEFINITIONS

In the description and tables, which follow, a number of terms are used. In order to provide a clear and consistent understanding of the specification and claims, including the scope to be given such terms, the following definitions are provided:

Genotype: Refers to the genetic composition of a cell or organism.

Plant: As used herein, the term "plant" includes reference to an immature or mature whole plant, including a plant that has been processed for steviol glycosides. Seed or plant part that will produce the plant is also considered to be the plant.

Plant Part: As used herein, the term "plant part" includes leaves, stems, roots, root tips, seed, embryo, pollen, ovules, flowers, root tips, shoots, microshoots, anthers, tissue, cells and the like.

Rebaudioside A: As used herein is a steviol glycoside that contains only glucose as its monosaccharide moieties. It contains four glucose molecules in total with the central glucose of the triplet connected to the main steviol structure at its hydroxyl group, and the remaining glucose at its carboxyl group forming an ester bond.

Rebaudioside D: As used herein is an ent-kaurane diterpene glycoside isolated from *Stevia rebaudiana*.

Rebaudioside M: As used herein is an ent-kaurane diterpene glycoside isolated from *Stevia rebaudiana*.

SNP: As used herein, the term "SNP" shall refer to a single nucleotide polymorphism.

Stevioside content: As used herein, stevioside is the percent glycoside derived from the stevia plant.

Traditional breeding techniques: Encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one carrot line or variety to another.

Vegetative propagation: "Vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, nodes, protoplasts, meristematic cell, root, root tip, pistil, anther, flower, shoot tip, shoot, stem, petiole, etc. When a whole plant is regenerated by vegetative propagation, it is also referred to as a vegetative propagation.

DETAILED DESCRIPTION

Stevia cultivar '16228013' is a *Stevia rebaudiana* plant variety, which has shown uniformity and stability, as described in the following Variety Description Information. It has been reproduced a sufficient number of generations with careful attention to uniformity of plant type. The cultivar has been increased with continued observation to uniformity.

Stevia cultivar '16228013' resulted from a biparental cross conducted in Ganzhou, Jiangxi Province, the People's Republic of China in September 2015 between the proprietary female Stevia variety '814011' (U.S. Pat. No. 9,668,451) and the proprietary male Stevia variety '44004' (unpatented elite high Rebaudioside M line).

Stevia cultivar '16228013' has the following morphologic and other characteristics from data taken in the Ganzhou, Jiangxi Province, People's Republic of China.

TABLE 1

VARIETY DESCRIPTION INFORMATION

Propagation type: Vegetative cuttings, tissue culture, and seed
Type: Perennial
Time to produce a rooted young plant: 20 to 30 days from a cutting
Root description: There are primary roots (including taproot and lateral root) and secondary roots (including fleshy root and rootlet)
Rooting habit: Fibrous root system, about 20.0 cm to 30.0 cm depth, 30.0 cm to 40.0 cm wide (in field conditions)
Plant and growth habit: Divided into 3 stages, vegetation growth stage, vegetation growth and reproductive growth together stage, reproductive growth stage
Plant height: 105.0 cm to 115.0 cm
Plant diameter: 57.0 cm to 69.0 cm
Stem length: 82.0 cm to 100.0 cm
Stem internode length: 2.7 cm to 4.0 cm
Stem diameter: 0.9 cm to 1.0 cm
Stem color: RHS 144B
Stem texture: Lignified at the base
Stem strength: strong
Stem anthocyanin: Absent
Stem, number of nodes on main stem: 40 to 50
Stem, number basal nodes per plant: 320 to 400
Lateral branch length: 10.0 cm to 35.0 cm
Lateral branch diameter: 0.15 cm to 0.25 cm
Lateral branch internode length: 3.0 cm to 5.0 cm
Lateral branch aspect: Upwards; at about 20 to 30 degree angle
Lateral branch strength: Strong
Lateral branch texture: Lignified at the base
Lateral branch color: RHS 142B
Leaf arrangement: Opposite
Leaf length: 8.0 cm to 10.0 cm
Leaf width: 1.5 cm to 2.8 cm
Leaf shape: Oval
Leaf apex: Abruptly tapered
Leaf base: Attenuate
Leaf margin: Shallow dentate
Leaf venation pattern: Netted venation
Leaf venation color: RHS 144B

TABLE 1-continued

VARIETY DESCRIPTION INFORMATION

Leaf texture (both upper and lower surfaces): Glabrous
Leaf color, immature, upper surface: RHS 137A
Leaf color, lower surface: RHS 138B
Leaf color, mature, upper surface: RHS 141B
Leaf color, mature, lower surface: RHS 138B
Bud length: 0.6 cm to 0.7 cm
Bud width: 0.2 cm to 0.3 cm
Bud shape: Ellipsoid
Bud color: Slightly RHS 142A (Green)
Inflorescence, appearance and arrangement: Flowers capitulum, consisting of five oblong bracts, five disk florets
Inflorescence, time to flower: About 110 days after transplant
Inflorescence, time of flowering: In Ganzhou, Jiangxi Province, the People's Republic of China, from August to September
Disc florets, length: 0.8 cm to 0.9 cm
Disc florets, width: 0.3 to 0.4 cm
Disc florets, shape: Tubulous
Disc florets, apex: Acute
Disc florets, margin: Smooth
Disc florets, base: Becomes tubulous at the middle to the base
Disc florets, color, upper surface: White
Disc florets, color, lower surface: White
Disc florets, venation color, upper surface: White
Disc florets, venation color, lower surface: White
Disc florets, bract length: 0.7 cm to 0.8 cm
Disc florets, bract width: 0.2 cm to 0.3 cm
Disc florets, bract shape: Lanceolate
Disc florets, bract apex: Abruptly tapered
Disc florets, bract margin: Smooth
Disc florets, bract base: Attenuate
Disc florets, bract color (both upper and lower surfaces): RHS 143C (Green)
Disc florets, bract venation color (both upper and lower surfaces): RHS 143C (Green)
Disc florets, bract fragrance: Absent
Stamen quantity: 5
Filament length: 0.20 cm to 0.25 cm
Filament color: RHS 145C
Anther shape: Column-like
Anther length: 0.16 cm to 0.21 cm
Anther color: RHS 150D
Pollen amount: 7000 to 8000
Pollen color: RHS 150D
Style length: 0.86 cm to 0.93 cm
Style color: RHS 144B
Stigma shape: 2-branched
Stigma color: RHS 145A
Ovary color: RHS 144C
Fruit and seed set: Seed are achenes, about 0.2 cm to 0.4 cm long, and 0.05 cm to 0.08 cm wide, with light brown pappus on the top.
Disease and insect/pest resistance: Good.

Comparison with Commercial Variety

'16228013' is most similar to its commercial parental line named '814011', which was deposited under CGMCC No. 9701. Differences between the two varieties are described in Table 2.

TABLE 2

Comparison with Similar Variety

| Characteristic | '16228013' | '814011' |
| --- | --- | --- |
| Leaf length | 8.0 cm to 10.0 cm | 8.0 cm to 11.0 cm |
| Leaf width | 1.5 cm to 2.8 cm | 2.1 cm to 2.5 cm |
| Cycle | 110 to 120 days | 101 to 110 days |
| Stevioside content | 0.39% | 0.38% |
| Rebaudioside A content | 6.43% | 8.45% |
| Rebaudioside D content | 2.39% | 1.11% |
| Rebaudioside M content | 1.59% | 1.12% |
| Performance (kilograms/hectare or kg/ha of harvested of dried leaves) | 4350 | 2700 |

Rebaudioside Content

To collect the data of Table 3 below, stevia leaf samples were air-dried/oven-dried before grinding into fine powder using a pestle and mortar. For each sample, leaf powder (100 mg) was extracted with 15 ml of 60° C. distilled water for 18 hours. The mixture was centrifuged and the supernatant filtered and collected for SG component analysis by HPLC (Agilent, USA). The analysis of steviol glycosides was carried out using an Agilent Technologies 1200 Series (USA) HPLC equipped with Poroshell 120 SB-C18 2.7 μm, 4.6×150 mm. A diode array set at 210 nm was used as the detector. In column one, Reb stands for Rebaudioside, Stev stands for Stevioside, and Dul stands for Dulcoside.

TABLE 3

Rebaudioside content of '16228013'

| Characteristic | '16228013' |
| --- | --- |
| Cycle | 110 to 120 days |
| Reb E content | 0.14% |
| Reb O content | 1.21% |
| Reb N content | 0.43% |
| Reb D content | 2.39% |
| Reb M content | 1.59% |
| Reb A content | 6.43% |
| Stev content | 0.39% |
| Reb F content | 0.12% |
| Reb C content | 0.49% |
| Dul A content | 0.00% |

Single Nucleotide Polymorphisms (SNPs) for identification of Stevia Cultivar '16228013'

Single nucleotide polymorphisms (SNPs) are variations in a particular single nucleotide that occurs at specific positions in the genome, which are the most common type of genetic variation among Stevia rebaudiana genomes. FIG. 1 shows that sequencing results indicated six SNPs are powerful molecular markers for the identification of variety '16228013'.

The genotypes of the six SNPs (SNP ID NO:1, SNP ID NO:2, SNP ID NO:3, SNP ID NO:4, SNP ID NO:5, and SNP ID NO:6) in Stevia variety '16228013' are listed as below.

TABLE 4

SNPs genotypes of '16228013'

| Variety | SNP No: 1 | SNP No: 2 | SNP No: 3 | SNP No: 4 | SNP No: 5 | SNP No: 6 |
| --- | --- | --- | --- | --- | --- | --- |
| 16228013 | GG | TC | CG | TC | TT | TT |

Another embodiment is a stevia plant or plant part derived from stevia variety '16228013' produced by crossing a plant or plant part of stevia variety '16228013' with another plant, wherein representative fresh tissue culture of said stevia variety '16228013' has been deposited and wherein said stevia plant part derived from the stevia variety '16228013' has 81%, 82%, 83%, 84%, 85%, 86%, 87%, 88%, 89%, 90%, 91%, 92%, 93%, 94%, 95%, 96%, 97%, 98%, 99% or 100% of the same polymorphisms for SNPs of SNP ID NO:1, SNP ID NO:2, SNP ID NO:3, SNP ID NO:4, SNP ID NO:5, and SNP ID NO:6 as the plant or plant part of stevia variety '16228013'.

A stevia seed derived from stevia variety '16228013' produced by crossing a plant or plant part of stevia variety '16228013' with another plant, wherein representative plant part of said stevia variety '16228013' has been deposited and wherein said stevia seed derived from the stevia variety '16228013' has essentially the same morphological characteristics as stevia variety '16228013' when grown in the same environmental conditions. The same environmental conditions may be, but are not limited to, a side-by-side comparison. The characteristics can be those listed in Table 1. The comparison can be made using any number of professionally accepted experimental designs and statistical analysis.

An embodiment is also directed to methods for producing a stevia plant by crossing a first parent stevia plant with a second parent stevia plant, wherein the first or second stevia plant is the stevia plant from the cultivar '16228013'. Further, both the first and second parent stevia plants may be the cultivar '16228013' (e.g., self-pollination). Therefore, any methods using the cultivar '16228013' are part of the embodiments of the invention: selfing, backcrosses, hybrid breeding, and crosses to populations. Any plants produced using cultivar '16228013' as parents are within the scope of the embodiments of the invention. As used herein, the term "plant" includes plant cells, plant protoplasts, plant cells of tissue culture from which stevia plants can be regenerated, plant calli, plant clumps, and plant cells that are intact in plants or parts of plants, such as pollen, flowers, embryos, ovules, seeds, leaves, stems, roots, anthers, pistils, shoots, microshoots, and the like. Thus, another aspect is to provide for cells which upon growth and differentiation produce a cultivar having essentially all of the physiological and morphological characteristics of '16228013'.

Another embodiment contemplates a stevia plant regenerated from a tissue culture of a cultivar (e.g., '16228013') or hybrid plant of the present embodiments of the invention. As is well-known in the art, tissue culture of stevia can be used for the in-vitro regeneration of a stevia plant. Tissue culture of various tissues of stevia and regeneration of plants therefrom is well known and widely published.

There are numerous steps in the development of any desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In stevia, the important traits leaf yield, earlier maturity, improved leaf quality, rebaudioside content, stevioside content, resistance to diseases and insects, resistance to drought and heat, and improved agronomic traits.

Breeding Methods

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to popular cultivars in environments representative of the commercial target area(s) for three or more years. The lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial stevia breeding program is to develop new, unique, and superior stevia cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic, and soil conditions and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new stevia cultivars.

Pureline cultivars of stevia are commonly bred by hybridization of two or more parents followed by selection. The complexity of inheritance, the breeding objectives, and the available resources influence the breeding method. Pedigree breeding, recurrent selection breeding, and backcross breeding are breeding methods commonly used in self-pollinated crops such as stevia. These methods refer to the manner in which breeding pools or populations are made in order to combine desirable traits from two or more cultivars or various broad-based sources. The procedures commonly used for selection of desirable individuals or populations of individuals are called mass selection, plant-to-row selection, and single seed descent or modified single seed descent. One or a combination of these selection methods can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an F1 (filial generation 1). An F2 population is produced by selfing F2 plants. Selection of desirable individual plants may begin as early as the F2 generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or to further select individual plants. Once a progeny row or progeny hill is selected as having desirable traits, it becomes what is known as a breeding line that is specifically identifiable from other breeding lines that were derived from the same original population. At an advanced generation (i.e., F5 or higher) seed of individual lines are evaluated in replicated testing. At an advanced stage the best lines or a mixture of phenotypically similar lines from the same original cross are tested for potential release as new cultivars.

The single seed descent procedure in the strict sense refers to planting a segregating population, harvesting one seed from every plant, and combining these seeds into a bulk, which is planted as the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using winter nurseries.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population.

Selection for desirable traits can occur at any segregating generation (F2 and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

In addition to phenotypic observations, the genotype of a plant can also be examined. There are many laboratory-based techniques available for the analysis, comparison, and characterization of plant genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs).

Breeding with Molecular Techniques

Isozyme Electrophoresis and RFLPs have been widely used to determine genetic composition. Shoemaker and Olsen, (Molecular Linkage Map of Soybean (Glycine max L. Merr.) pp. 6.131-6.138 in S. J. O'Brien (Ed.) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (Eds.), DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., Theor. Appl. Genet., 95:22-225 (1997). SNPs may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation Breeding

Mutation breeding is another method of introducing new traits into stevia varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethylenamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company (1993).

Production of Double Haploids

The production of double haploids can also be used for the development of homozygous varieties in a breeding program. Double haploids are produced by the doubling of a set of chromosomes from a heterozygous plant to produce a completely homozygous individual. For example, see Wan, et al., Theor. Appl. Genet., 77:889-892 (1989).

Descriptions of other breeding methods that are commonly used for different traits and crops can be found in one of several reference books (e.g., Allard (1960); Simmonds (1979); Sneep, et al. (1979); Fehr (1987)).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and to the grower, processor, and consumer, for special advertising, marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

The stevia flower is monoecious in that the male and female structures are in the same flower. The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation (F1) hybrid seed. Planting of this seed produces F1 hybrid plants of which half their genetic component is from the female parent and half from the male parent. Segregation of genes begins at meiosis thus producing second generation (F2) seed. Assuming multiple genetic differences between the original parents, each F2 seed has a unique combination of genes.

Further Embodiments

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, in particular embodiments, also relates to transformed versions of the claimed cultivar.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed stevia plants, using transformation methods as described below to incorporate transgenes into the genetic material of the stevia plant(s).

Expression Vectors for Stevia Transformation: Marker Genes

Expression vectors include at least one genetic marker operably linked to a regulatory element (for example, a promoter) that allows transformed cells containing the marker to be either recovered by negative selection (i e, inhibiting growth of cells that do not contain the selectable marker gene), or by positive selection (i.e., screening for the product encoded by the genetic marker). Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals, confers resistance to kanamycin. Fraley, et al., PNAS, 80:4803 (1983). Another commonly used selectable marker gene is the hygromycin phosphotransferase gene which confers resistance to the antibiotic hygromycin. Vanden Elzen, et al., Plant Mol. Biol., 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986). Other selectable marker genes confer resistance to herbicides such as glyphosate, glufosinate, or bromoxynil. Comai, et al., Nature, 317:741-744 (1985); Gordon-Kamm, et al., Plant Cell, 2:603-618 (1990); and Stalker, et al., Science, 242:419-423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz, et al., Somatic Cell Mol. Genet., 13:67 (1987); Shah, et al., Science, 233:478 (1986); Charest, et al., Plant Cell Rep., 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include ß-glucuronidase (GUS), ß-galactosidase, luciferase, and chloramphenicol acetyltransferase. Jefferson, R. A., Plant Mol. Biol. Rep., 5:387 (1987); Teeri, et al., EMBO J., 8:343 (1989); Koncz, et al., PNAS, 84:131 (1987); DeBlock, et al., EMBO J. 3:1681 (1984).

In-vivo methods for visualizing GUS activity that do not require destruction of plant tissue are available. Molecular Probes Publication 2908, IMAGENE GREEN, pp. 1-4 (1993) and Naleway, et al., J. Cell Biol., 115:151a (1991). However, these in-vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., Science, 263:802 (1994). GFP and mutants of GFP may be used as screenable markers Expression Vectors for Stevia Transformation: Promoters Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in stevia. Optionally, the inducible promoter is operably linked to a nucleotide sequence encoding a signal sequence which is operably linked to a gene for expression in stevia. With an inducible promoter the rate of transcription increases in response to an inducing agent.

Any inducible promoter can be used in the embodiments of the instant invention. See Ward, et al., Plant Mol. Biol., 22:361-366 (1993). Exemplary inducible promoters include, but are not limited to, that from the ACEI system which responds to copper (Mett, et al., PNAS, 90:4567-4571 (1993)); In2 gene from maize which responds to benzenesulfonamide herbicide safeners (Hershey, et al., Mol. Gen. Genet., 227:229-237 (1991) and Gatz, et al., Mol. Gen. Genet., 243:32-38 (1994)); or Tet repressor from Tn10 (Gatz, et al., Mol. Gen. Genet., 227:229-237 (1991)). An example inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., PNAS, 88:0421 (1991)).

B. Constitutive Promoters:

A constitutive promoter is operably linked to a gene for expression in stevia or the constitutive promoter is operably linked to a nucleotide sequence encoding a signal sequence which is operably linked to a gene for expression in stevia.

Many different constitutive promoters can be utilized in the embodiments of the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)); and maize H3 histone (Lepetit, et al., Mol. Gen. Genet., 231:276-285 (1992) and Atanassova, et al., Plant Journal, 2 (3): 291-300 (1992)).

The ALS promoter, Xbal/Ncol fragment 5' to the Brassica napus ALS3 structural gene (or a nucleotide sequence similarity to said Xbal/Ncol fragment), represents a particularly useful constitutive promoter. See PCT Application No. WO 96/30530.

C. Tissue-Specific or Tissue-Preferred Promoters:

A tissue-specific promoter is operably linked to a gene for expression in stevia. Optionally, the tissue-specific promoter is operably linked to a nucleotide sequence encoding a signal sequence which is operably linked to a gene for expression in stevia. Plants transformed with a gene of interest operably linked to a tissue-specific promoter produce the protein product of the transgene exclusively, or preferentially, in a specific tissue.

Any tissue-specific or tissue-preferred promoter can be utilized in the embodiments of the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter, such as that from cab or rubisco (Simpson, et al., EMBO J., 4(11): 2723-2729 (1985) and Timko, et al., Nature, 318:579-582 (1985)); an anther-specific promoter, such as that from LAT52 (Twell, et al., Mol. Gen. Genet., 217:240-245 (1989)); a pollen-specific promoter, such as that from Zm13

(Guerrero, et al., Mol. Gen. Genet., 244:161-168 (1993)); or a microspore-preferred promoter, such as that from apg (Twell, et al., Sex. Plant Reprod., 6:217-224 (1993)).

Signal Sequences for Targeting Proteins to Subcellular Compartments

Transport of protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., Cell, 39:499-509 (1984); Steifel, et al., Plant Cell, 2:785-793 (1990).

Foreign Protein Genes and Agronomic Genes

With transgenic plants, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem., 114:92-6 (1981).

According to an embodiment, the transgenic plant provided for commercial production of foreign protein is a stevia plant. In another embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Glick and Thompson, Methods in Plant Molecular Biology and Biotechnology, CRC Press, Boca Raton, 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, Agronomic Genes can be Expressed in Transformed Plants. More Particularly, plants can be genetically engineered to express various phenotypes of agronomic interest. Exemplary genes implicated in this regard include, but are not limited to, those categorized below:

A. Genes that Confer Resistance to Pests or Disease and that Encode:

1. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); Mindrinos, et al., Cell, 78:1089 (1994) (*Arabidopsis* RSP2 gene for resistance to *Pseudomonas syringae*).

2. A gene conferring resistance to a pest, such as nematodes. See, e.g., PCT Application No. WO 96/30517; PCT Application No. WO 93/19181.

3. A *Bacillus thuringiensis* protein, a derivative thereof or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding 0.8-endotoxin genes can be purchased from American Type Culture Collection, Manassas, Va., for example, under ATCC Accession Nos. 40098, 67136, 31995, and 31998.

4. A lectin. See, for example, the disclosure by Van Damme, et al., Plant Molec. Biol., 24:25 (1994), who disclose the nucleotide sequences of several *Clivia miniata* mannose-binding lectin genes.

5. A vitamin-binding protein such as avidin. See PCT Application No. US 93/06487. The application teaches the use of avidin and avidin homologues as larvicides against insect pests.

6. An enzyme inhibitor, for example, a protease or proteinase inhibitor or an amylase inhibitor. See, for example, Abe, et al., J. Biol. Chem., 262:16793 (1987) (nucleotide sequence of rice cysteine proteinase inhibitor); Huub, et al., Plant Molec. Biol., 21:985 (1993) (nucleotide sequence of cDNA encoding tobacco proteinase inhibitor I); Sumitani, et al., Biosci. Biotech. Biochem., 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

7. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

8. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266, 317 to Tomalski, et al., who disclose genes encoding insect-specific, paralytic neurotoxins.

9. An insect-specific venom produced in nature by a snake, a wasp, etc. For example, see Pang, et al., Gene, 116:165 (1992), for disclosure of heterologous expression in plants of a gene coding for a scorpion insectotoxic peptide.

10. An enzyme responsible for a hyper-accumulation of a monoterpene, a sesquiterpene, a steroid, a hydroxamic acid, a phenylpropanoid derivative, or another non-protein molecule with insecticidal activity.

11. An enzyme involved in the modification, including the post-translational modification, of a biologically active molecule. For example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Molec. Biol., 23:691 (1993), who teach the nucleotide sequence of a cDNA encoding tobacco hornworm chitinase, and Kawalleck, et al., Plant Molec. Biol., 21:673 (1993), who provide the nucleotide sequence of the parsley ubi4-2 polyubiquitin gene.

12. A molecule that stimulates signal transduction. For example, see the disclosure by Botella, et al., Plant Molec. Biol., 24:757 (1994), of nucleotide sequences for mung bean calmodulin cDNA clones and Griess, et al., Plant Physiol., 104:1467 (1994), who provide the nucleotide sequence of a maize calmodulin cDNA clone.

13. A hydrophobic moment peptide. See PCT Application No. WO 95/16776 (disclosure of peptide derivatives of Tachyplesin which inhibit fungal plant pathogens) and PCT Application No. WO 95/18855 (teaches synthetic antimicrobial peptides that confer disease resistance).

14. A membrane permease, a channel former or a channel blocker. For example, see the disclosure of Jaynes, et al., Plant Sci., 89:43 (1993), of heterologous expression of a cecropin-ß-lytic peptide analog to render transgenic tobacco plants resistant to *Pseudomonas solanacearum*.

15. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

16. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Intl Symposium on Molecular Plant-Microbe Interactions (Edinburgh, Scotland) (1994) (enzymatic inactivation in transgenic tobacco via production of single-chain antibody fragments).

17. A virus-specific antibody. See, for example, Tavladoraki, et al., Nature, 366:469 (1993), who show that transgenic plants expressing recombinant antibody genes are protected from virus attack.

18. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., Bio/technology, 10:1436 (1992). The cloning and characterization of a gene which encodes a bean endopolygalacturonase-inhibiting protein is described by Toubart, et al., Plant J., 2:367 (1992).

19. A developmental-arrestive protein produced in nature by a plant. For example, Logemann, et al., Bio/technology, 10:305 (1992), have shown that transgenic plants expressing the barley ribosome-inactivating gene have an increased resistance to fungal disease.

B. Genes that Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., EMBO J., 7:1241 (1988), and Miki, et al., Theor. Appl. Genet., 80:449 (1990), respectively. Other herbicides such as dicamba increase plant growth.

2. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada, et al., and U.S. Pat. No. 4,975,374 to Goodman, et al., disclose nucleotide sequences of glutamine synthetase genes which confer resistance to herbicides such as L-phosphinothricin or cyclohexanedione. The nucleotide sequence of a PAT gene is provided in European Application No. 0 242 246 to Leemans, et al. DeGreef, et al., Bio/technology, 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2, and Acc1-S3 genes described by Marshall, et al., Theor. Appl. Genet., 83:435 (1992).

3. An herbicide that inhibits photosynthesis, such as a triazine (psbA and gs+ genes) bromoxynil or a benzonitrile (nitrilase gene). Przibila, et al., Plant Cell, 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., Biochem. J., 285:173 (1992).

C. Genes that Confer or Contribute to a Value-Added Trait, Such as:

1. Modified fatty acid metabolism, for example, by transforming a plant with an antisense gene of stearyl-ACP desaturase to increase stearic acid content of the plant. See Knultzon, et al., PNAS, 89:2624 (1992).

2. Decreased phytate content: (a) Introduction of a phytase-encoding gene would enhance breakdown of phytate, adding more free phosphate to the transformed plant. See, for example, Van Hartingsveldt, et al., Gene, 127:87 (1993), for a disclosure of the nucleotide sequence of an *Aspergillus niger* phytase gene; and (b) A gene could be introduced that reduced phytate content. For example, in maize, this could be accomplished by cloning and then reintroducing DNA associated with the single allele, which is responsible for maize mutants characterized by low levels of phytic acid. See, Raboy, et al., Maydica, 35:383 (1990).

3. Modified carbohydrate composition effected, for example, by transforming plants with a gene coding for an enzyme that alters the branching pattern of starch. See, Shiroza, et al., J. Bacteol., 170:810 (1988) (nucleotide sequence of *Streptococcus* mutants fructosyltransferase gene); Steinmetz, et al., Mol. Gen. Genet., 20:220 (1985)

(nucleotide sequence of *Bacillus subtilis* levansucrase gene); Pen, et al., Bio/technology, 10:292 (1992) (production of transgenic plants that express *Bacillus licheniformis* α-amylase); Elliot, et al., Plant Molec. Biol., 21:515 (1993) (nucleotide sequences of tomato invertase genes); Sorgaard, et al., J. Biol. Chem., 268:22480 (1993) (site-directed mutagenesis of barley α-amylase gene); and Fisher, et al., Plant Physiol., 102:1045 (1993) (maize endosperm starch branching enzyme II).

4. Modified fiber characteristics, such as fiber quality represent another example of a trait that may be modified in stevia varieties. For example, U.S. Pat. No. 6,472,588 describes transgenic plants transformed with a sucrose phosphate synthase nucleic acid to alter fiber characteristics such as strength, length, fiber fineness, fiber maturity ratio, immature fiber content, fiber uniformity, and micronaire. Stevia plants comprising one or more genes coding for an enzyme selected from the group consisting of endoxyloglucan transferase, catalase and peroxidase for the improvement of fiber characteristics are also described in U.S. Pat. No. 6,563,022. Stevia fiber modification using ovary-tissue transcriptional factors preferentially directing gene expression in ovary tissue, particularly in very early fruit development, utilized to express genes encoding isopentenyl transferase in stevia ovule tissue and modify the characteristics of boll set in plants and alter fiber quality characteristics including fiber dimension and strength is discussed in U.S. Pat. No. 6,329,570. A gene controlling the fiber formation mechanism in plants is described in U.S. Pat. No. 6,169,174. Genes involved in lignin biosynthesis are described in U.S. Pat. No. 5,451,514.

Methods for Stevia Transformation

Numerous methods for plant transformation have been developed, including biological and physical, plant transformation protocols. See, for example, Mild, et al., "Procedures for Introducing Foreign DNA into Plants" in Methods in Plant Molecular Biology and Biotechnology, Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson (Eds.), CRC Press, Inc., Boca Raton, pp. 89-119 (1993).

A. Agrobacterium-Mediated Transformation:

One method for introducing an expression vector into plants is based on the natural transformation system of Agrobacterium. See, for example, Horsch, et al., Science, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for Agrobacterium-mediated gene transfer are provided by Gruber, et al., supra, Miki, et al., supra, and Moloney, et al., Plant Cell Rep., 8:238 (1989). See also, U.S. Pat. No. 5,563,055 (Townsend and Thomas), issued Oct. 8, 1996.

B. Direct Gene Transfer:

Several methods of plant transformation, collectively referred to as direct gene transfer, have been developed as an alternative to Agrobacterium-mediated transformation. A generally applicable method of plant transformation is microprojectile-mediated transformation wherein DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Sanford, et al., Part. Sci. Technol., 5:27 (1987); Sanford, J. C., Trends Biotech., 6:299 (1988); Klein, et al., Bio/technology, 6:559-563 (1988); Sanford, J. C., Physiol Plant, 7:206 (1990); Klein, et al., Bio/technology, 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., Bio/technology, 9:996 (1991). Alternatively, liposome and spheroplast fusion have been used to introduce expression vectors into plants. Deshayes, et al., EMBO J., 4:2731 (1985); Christou, et al., PNAS, 84:3962 (1987). Direct uptake of DNA into protoplasts using $CaCl_2$ precipitation, polyvinyl alcohol, or poly-L-ornithine has also been reported. Hain, et al., Mol. Gen. Genet., 199:161 (1985) and Draper, et al., Plant Cell Physiol. 23:451 (1982). Electroporation of protoplasts and whole cells and tissues has also been described. Donn, et al., In Abstracts of VIIth International Congress on Plant Cell and Tissue Culture IAPTC, A2-38, p. 53 (1990); D'Halluin, et al., Plant Cell, 4:1495-1505 (1992); and Spencer, et al., *Plant Mol. Biol.*, 24:51-61 (1994).

Following transformation of stevia target tissues, expression of the above-described selectable marker genes allows for preferential selection of transformed cells, tissues, and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular stevia cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

C. Single-Gene Conversion

When the term "stevia plant" is used herein, this also includes any single gene conversions of that variety. The term "single gene converted plant" as used herein refers to those stevia plants which are developed by a plant breeding technique called backcrossing wherein essentially all of the desired morphological and physiological characteristics of a variety are recovered in addition to the single gene transferred into the variety via the backcrossing technique. Backcrossing methods can be used herein to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental stevia plant which contributes the gene for the desired characteristic is termed the "nonrecurrent" or "donor parent". This terminology refers to the fact that the nonrecurrent parent is used one time in the backcross protocol and therefore does not recur. The parental stevia plant to which the gene or genes from the nonrecurrent parent are transferred is known as the recurrent parent as it is used for several rounds in the backcrossing protocol (Poehlman &

Sleper (1994); Fehr (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a stevia plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185; 5,973,234; and 5,977,445, the disclosures of which are specifically hereby incorporated by reference.

D. Genome Editing

Genome editing technologies such as clustered regularly interspaced short palindromic repeat (CRISPR)-CRISPR associated protein (CRISPR-Cas) allow targeted modification of almost any crop genomic sequences to generate novel variations, which has facilitated targeted trait improvement in plants. Recently, CRISPR from Prevotella and Francisella 1 (Cpf1) has emerged as a new tool for efficient genome editing, including DNA-free genome editing in plants. CRISPR-Cpf1 system has shown the potential of higher efficiency, higher specificity, and wider applications than the CRISPR-Cas9 system.

Further reproduction of the variety can occur by tissue culture and regeneration. Tissue culture of various tissues of stevia and regeneration of plants therefrom is well known and widely published. For example, reference may be had to Komatsuda, T., et al., Crop Sci., 31:333-337 (1991); Stephens, P. A., et al., Theor. Appl. Genet., 82:633-635 (1991); Komatsuda, T., et al., Plant Cell, Tissue and Organ Culture, 28:103-113 (1992); Dhir, S., et al. Plant Cell Rep., 11:285-289 (1992); Pandey, P., et al., Japan J. Breed., 42: 1-5 (1992); and Shetty, K., et al., Plant Science, 81:245-251 (1992); as well as U.S. Pat. No. 5,024,944 issued Jun. 18, 1991 to Collins, et al., and U.S. Pat. No. 5,008,200 issued Apr. 16, 1991 to Ranch, et al. Thus, another aspect of the invention is to provide cells which upon growth and differentiation produce stevia plants having the physiological and morphological characteristics of stevia cultivar '16228013'.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185; 5,973,234; and U.S. Pat. No. 5,977,445, described certain techniques.

Another embodiment is directed to methods for producing a stevia plant by crossing a first parent stevia plant with a second parent stevia plant wherein the first or second parent stevia plant is a stevia plant of the cultivar '16228013'. Further, both first and second parent stevia plants can come from the stevia cultivar '16228013'. Thus, any such methods using the stevia cultivar '16228013' are part of the embodiments of the invention: selfing, backcrosses, hybrid production, crosses to populations, and the like. All plants produced using stevia cultivar '16228013' as a parent are within the scope of the embodiments of the invention, including those developed from varieties derived from stevia cultivar '16228013'. Advantageously, the stevia cultivar could be used in crosses with other, different, stevia plants to produce first generation (F1) stevia hybrid seeds and plants with superior characteristics. The cultivar of the embodiments of the invention can also be used for transformation where exogenous genes are introduced and expressed by the cultivar of the embodiments of the invention. Genetic variants created either through traditional breeding methods using cultivar '16228013' or through transformation of '16228013' by any of a number of protocols known to those of skill in the art are intended to be within the scope of the embodiments of the invention.

The following describes breeding methods that may be used with cultivar '16228013' in the development of further stevia plants. One such embodiment is a method for developing a '16228013' progeny stevia plant in a stevia plant breeding program comprising: obtaining the stevia plant, or a part thereof, of cultivar '16228013', utilizing said plant or plant part as a source of breeding material, and selecting a '16228013' progeny plant with molecular markers in common with '16228013' and/or with morphological and/or physiological characteristics selected from the characteristics listed in Tables 1, 2, 3, 4, 5, 6, 7, 8, or 9. Breeding steps that may be used in the stevia plant breeding program include pedigree breeding, backcrossing, mutation breeding, and recurrent selection. In conjunction with these steps, techniques such as marker-enhanced selection, genetic marker enhanced selection (for example, SSR markers), and the making of double haploids may be utilized.

Another method involves producing a population of cultivar '16228013' progeny stevia plants, comprising crossing cultivar '16228013' with another stevia plant, thereby producing a population of stevia plants, which, on average, derive 50% of their alleles from cultivar '16228013'. A plant of this population may be selected and repeatedly selfed or sibbed with a stevia cultivar resulting from these successive filial generations. One embodiment of this invention is the stevia cultivar produced by this method and that has obtained at least 50% of its alleles from cultivar '16228013'.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). Thus the embodiments of the invention includes stevia cultivar '16228013' progeny stevia plants comprising a combination of at least two '16228013' traits selected from the group consisting of those listed in Tables 1, 2, 3, 4, 5, 6, 7, 8, or 9 or the '16228013' combination of traits listed in the Summary, so that said progeny stevia plant is not significantly different for said traits than stevia cultivar '16228013' as determined at the 5% significance level when grown in the same environment. Using techniques described herein, molecular markers may be used to identify said progeny plant as a '16228013' progeny plant. Mean trait values may be used to determine whether trait differences are significant, and the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar '16228013' may also be characterized through their filial relationship with stevia cultivar '16228013', as for example, being within a certain number of breeding crosses of stevia cultivar '16228013'. A breeding cross is a cross made to introduce new genetics into the progeny, and is distinguished from a cross, such as a self or a sib cross, made to select among existing genetic alleles. The lower the number of breeding crosses in the pedigree, the closer the relationship between stevia cultivar '16228013' and its progeny. For example, progeny produced by the methods described herein may be within 1, 2, 3, 4 or 5 breeding crosses of stevia cultivar '16228013'.

As used herein, the term "plant" includes plant cells, plant protoplasts, plant cell tissue cultures from which stevia plants can be regenerated, plant calli, plant clumps, and plant cells that are intact in plants or parts of plants, such as embryos, pollen, ovules, flowers, leaves, roots, root tips, anthers, pistils, and the like.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One embodiment may be embodied in other specific forms without departing from its spirit or essential characteristics. The described embodiments are to be considered in all respects only as illustrative and not restrictive. All changes which come within the meaning and range of equivalency of the claims are to be embraced within their scope.

Various embodiments, include components, methods, processes, systems and/or apparatus substantially as depicted and described herein, including various embodiments, sub-combinations, and subsets thereof. Those of skill in the art will understand how to make and use an embodiment(s) after understanding the present disclosure.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the embodiment(s) requires more features than are expressly recited in each claim. Rather, as the following claims reflect, inventive aspects lie in less than all features of a single foregoing disclosed embodiment. Thus, the following claims are hereby incorporated into this Detailed Description.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed.

DEPOSIT INFORMATION

A deposit of plant tissue of the stevia variety named '16228013' disclosed above and recited in the appended claims has been made with and accepted under the Budapest Treaty with the China General Microbiological Culture Collection Center (CGMCC), Institute of Microbiology, Chinese Academy of Sciences, Datun Road, Chaoyang District 100101 China. The date of deposit was Dec. 12, 2018. The CGMCC Accession Number is CGMCC No. 16984. The deposit of plant tissue was taken from the same deposit maintained by Applicant since prior to the filing date of this application. The deposit will be maintained in the CGMCC depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A method of determining the genotype of a stevia plant, wherein said method comprises:
   obtaining a sample of nucleic acids from said plant; and
   detecting in said nucleic acids, one or more single nucleotide polymorphisms (SNPs) comprising SEQ ID NO:1, SEQ ID NO:2, SEQ ID NO:3, SEQ SID NO:4, SEQ ID NO:5, and SEQ ID NO:6.

* * * * *

SEQUENCE LISTING

<160> NUMBER OF SEQ ID NOS: 6

<210> SEQ ID NO 1
<211> LENGTH: 102
<212> TYPE: DNA
<213> ORGANISM: Stevia rebaudiana
<220> FEATURE:
<221> NAME/KEY: variation
<222> LOCATION: (56)..(56)
<223> OTHER INFORMATION: Where "R" is either "G" or "A"

<400> SEQUENCE: 1
aaaaatagac tttttaccat ctcttcctct caagtctcaa tctcaacacc tacacrtgta    60
tgttttttca aacaaaccac acacattggt tttgatctaa aa                      102

<210> SEQ ID NO 2
<211> LENGTH: 102
<212> TYPE: DNA
<213> ORGANISM: Stevia rebaudiana
<220> FEATURE:
<221> NAME/KEY: variation
<222> LOCATION: (61)..(61)
<223> OTHER INFORMATION: Where "Y" is either "C" or "T"

<400> SEQUENCE: 2
ggtaataaca accttagttg cctaattata tatgcttctt gtgatgaatt tccaatctaa    60
ytgtacttga gctaatatag aaaacctagt tgctgccaca tt                      102

<210> SEQ ID NO 3
<211> LENGTH: 95
<212> TYPE: DNA
<213> ORGANISM: Stevia rebaudiana
<220> FEATURE:
<221> NAME/KEY: variation
<222> LOCATION: (52)..(52)
<223> OTHER INFORMATION: Where "S" is either "G" or "C"

<400> SEQUENCE: 3
gattggtaat tggaagtgtt gtttattaca tatggcaaga gaggaacctt asattgtttc    60
aaggtaagtc tcgtggttat gatgatgtgt gcaag                              95

<210> SEQ ID NO 4
<211> LENGTH: 98
<212> TYPE: DNA
<213> ORGANISM: Stevia rebaudiana
<220> FEATURE:
<221> NAME/KEY: variation
<222> LOCATION: (49)..(49)
<223> OTHER INFORMATION: Where "Y" is either "T" or "C"

<400> SEQUENCE: 4
aaaatggaaa cattttcttt ttacatttca gcatctgagt tgactcggyt gcaatcacaa    60
atatgtggaa aaaatggtga tcaccaagtt ccagagtt                           98

<210> SEQ ID NO 5
<211> LENGTH: 103
<212> TYPE: DNA
<213> ORGANISM: Stevia rebaudiana
<220> FEATURE:
<221> NAME/KEY: variation
<222> LOCATION: (49)..(49)
<223> OTHER INFORMATION: Where "W" is either "A" or "T"

<400> SEQUENCE: 5
atggaagatg aacctgatgt tcctgaacaa ctcgttcgcc gatcggttwg tctcgaaatc    60

```
cattcacaag ttctttata ttgcactgat ttgatactta ggg                      103
```

<210> SEQ ID NO 6
<211> LENGTH: 101
<212> TYPE: DNA
<213> ORGANISM: Stevia rebaudiana
<220> FEATURE:
<221> NAME/KEY: variation
<222> LOCATION: (48)..(48)
<223> OTHER INFORMATION: Where "Y" is either "C" or "T"

<400> SEQUENCE: 6

```
agaagaacag tgccagaata atctgtggcg ctaaagtgat ccaaccayac ccttgttctc    60
ccagttatat aaaagattaa aaattgctag ttgtccttcg c                       101
```